US00PP31327P2

(12) United States Plant Patent
Li

(10) Patent No.: US PP31,327 P2
(45) Date of Patent: Jan. 7, 2020

(54) ***VERBENA* PLANT NAMED 'KLEVP18010'**

(50) Latin Name: ***Verbena* x *hybrida***
Varietal Denomination: KLEVP18010

(71) Applicant: Klemm+Sohn GmbH & Co. KG, Stuttgart (DE)

(72) Inventor: Ruijun Li, North Parramatta (AU)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 0 days.

(21) Appl. No.: 16/501,438

(22) Filed: Apr. 16, 2019

(51) Int. Cl.
*A01H 5/02* (2018.01)
*A01H 6/86* (2018.01)

(52) U.S. Cl.
USPC ..... Plt./308

(58) Field of Classification Search
USPC ..... Plt./308
CPC ..... A01H 5/02; A01H 6/86
See application file for complete search history.

*Primary Examiner* — Annette H Para
(74) *Attorney, Agent, or Firm* — Barbara Campbell; James M. Weatherly; Cochran Freund & Young LLC

(57) ABSTRACT

A new *verbena* plant particularly distinguished by pink and white bi-colored flowers, an upright growth habit, and good tolerance to powdery mildew, is disclosed.

1 Drawing Sheet

Genus and species: *Verbena* x *hybrida*.
Variety denomination: 'KLEVP18010'.

BACKGROUND OF THE NEW PLANT

The present invention comprises a new and distinct variety of *verbena*, botanically known as *Verbena* x *hybrida*, and hereinafter referred to by the variety name 'KLEVP18010'. 'KLEVP18010' originated from a cross-pollination conducted in February 2014 in Cobbitty, New South Wales, Australia between the proprietary female *verbena* variety 'VC13.0040' (unpatented), and the proprietary male *verbena* variety 'VC13.0078.1' (unpatented).

The seeds from the cross were sown and plants were grown for evaluation, where an individual plant designated 'KLEVP18010' was selected from the group of plants in Cobbitty, New South Wales, Australia in October 2014.

In October 2014, 'KLEVP18010' was first vegetatively propagated by vegetative cuttings in Cobbitty, New South Wales, Australia. 'KLEVP18010' was found to reproduce true to type in successive generations of asexual propagation via vegetative stem cuttings.

SUMMARY

The following are the most outstanding and distinguishing characteristics of this new variety when grown under normal horticultural practices in Cobbitty, New South Wales, Australia.

1. Pink and white bi-colored flowers;
2. An upright habit; and
3. Good tolerance to powdery mildew.

DESCRIPTION OF THE PHOTOGRAPH

This new *verbena* plant is illustrated by the accompanying photograph which shows the plant's overall plant habit including form, foliage, and flowers. The photograph is of a plant approximately five months old grown outdoors in Stuttgart, Germany in July 2017. The colors shown are as true as can be reasonably obtained by conventional photographic procedures.

DESCRIPTION OF THE NEW VARIETY

The following detailed descriptions set forth the distinctive characteristics of 'KLEVP18010'. The data which define these characteristics were collected from asexual reproductions carried out in Stuttgart, Germany. Data was collected on three-month-old plants grown in a greenhouse in Stuttgart, Germany in June 2017. Color references are to The R.H.S. Colour Chart of The Royal Horticultural Society of London (R.H.S.), 5$^{th}$ edition (2007).

Classification:
- *Family*.—Verbenaceae.
- *Botanical*.—*Verbena* x *hybrida*.
- *Common*.—*Verbena*.
- *Designation*.—'KLEVP18010'.

Parentage:
- *Female parent*.—'VC13.0040' (unpatented).
- *Male parent*.—'VC13.0078.1' (unpatented).

Plant:
- *Growth and branching habit*.—Upright.
- *Height* (*from top of soil*).—31 cm.
- *Width* (*horizontal plant diameter*).—27 cm.
- *Time to produce a finished flowering plant*.—Approximately 8 weeks.
- *Time to initiate and develop roots*.—3 weeks.
- *Root description*.—White, RHS 155B, Fine fibrous roots.

Stems:
- *Number of branches per plant*.—More than 24.
- *Length*.—21 cm.
- *Diameter*.—0.23 cm.
- *Internode length*.—Approximately 2.1 cm.
- *Color*.—RHS 139D.
- *Anthocyanin*.—Absent.
- *Texture and appearance*.—Pubescent, round.

Leaves:
*Arrangement*.—Opposite.
*Immature and mature leaf color*.—Upper surface: RHS 141A. Lower surface: RHS 141C.
*Length*.—2.4 cm.
*Width*.—1.4 cm.
*Shape*.—Lanceolate.
*Apex*.—Acute.
*Base*.—Obtuse.
*Margin*.—Crenate.
*Texture*.—Upper surface: Leathery. Lower surface: Rugose.
*Venation type*.—Pinnate.
*Venation color* (*both upper and lower surfaces*).—RHS 141D.
*Petioles*.—Length: 0.3 cm. Diameter: 0.1 cm. Color: RHS 141D. Texture: Leathery.

Flower buds:
*Shape*.—Tall, cylindrical.
*Length*.—0.5 cm.
*Diameter*.—0.2 cm.
*Color* (*at tight bud*).—RHS N57D.

Inflorescence:
*Blooming habit* (*flowering season*).—Continuously.
*Lastingness of individual blooms on the plant*.—1 week.
*Fragrance*.—Absent.
*Inflorescence type*.—Umbel.
*Length of inflorescence*.—4.3 cm.
*Diameter of inflorescence*.—4.1 cm.
*Number of florets per inflorescence*.—Average of 22.
*Peduncle*.—Color: RHS 141A. Length: 1.1 cm. Diameter: 0.1 cm.

Florets:
*Length*.—2.4 cm.
*Diameter*.—2.3 cm.
*Texture*.—Smooth.
*Form*.—Single.
*Corolla tube length*.—1.7 cm.
*Corolla tube color*.—RHS 56C.
*Petals*.—Length of lobe: 1.4 cm. Diameter of lobe: 1.1 cm. Lobe shape: Obtuse. Apex: Emarginate. Base: Fused. Margin: Entire. Texture (both upper and lower surfaces): Glossy, satiny. Color: Immature: Upper surface: RHS 61C. Lower surface: RHS N57D. Mature: Upper surface: RHS 64D. Lower surface: RHS 68C.
*Pedicels*.—Not visible.

Sepals:
*Shape*.—Lanceolate.
*Apex*.—Acute.
*Base*.—Fused.
*Margin*.—Entire.
*Length*.—1.2 cm.
*Diameter*.—0.2 cm.
*Color*.—RHS 141C.
*Texture* (*both upper and lower surfaces*).—Hairy, dull.

Reproductive organs:
*Stamens*.—Present. Quantity: 4. Appearance: Shiny. Color: RHS 139D. Filament length: 0.3 cm. Filament diameter: 0.1 cm. Anther: Shape: Bilobed, ovate. Color: RHS 141D. Length: 0.2 cm. Diameter: 0.1 cm. Pollen amount: Sparse. Pollen color: Cream RHS 150D.
*Pistils*.—Quantity: 1. Length: 1 cm. Diameter: 0.1 cm. Stigma: Color: RHS 141D. Appearance: Ovate. Length: 0.1 cm. Diameter: 0.1 cm. Style: Color: RHS 141D. Length: 0.9 cm. Diameter: 0.1 cm. Appearance: Long.

Fruit and seed set: None observed.

Disease and pest/insect resistance: Good tolerance to powdery mildew (*Podosphaera xanthii*).

COMPARISON WITH PARENTAL LINES AND KNOWN VARIETY

'KLEVP18010' is distinguished from its parents as described in Table 1.

TABLE 1

Comparison with Parental Lines

| Characteristic | 'KLEVP18010' | Female parent | Male parent |
|---|---|---|---|
| Flower color | Pink and white bi-color | Orange | Grey with red eyes |
| Branching | Average number is 18 | Average number is 18 | Average number is 14 |

'KLEVP18010' is most similar to the commercial *verbena* POPS 'Salmon+Red Eye' (also known as 'KLEVP15616', U.S. Plant Pat. No. 28,320). Differences between the varieties are described in Table 2.

TABLE 2

Comparison with Similar Variety

| Characteristic | 'KLEVP18010' | 'Salmon + Red Eye' |
|---|---|---|
| Flower color | Pink with small cream white eyes and white margins | Pink with a dark red center |
| Flower shape | Star shaped | Round shape with overlapping petals |

I claim:

1. A new and distinct variety of *verbena* plant designated 'KLEVP18010' as illustrated and described herein.

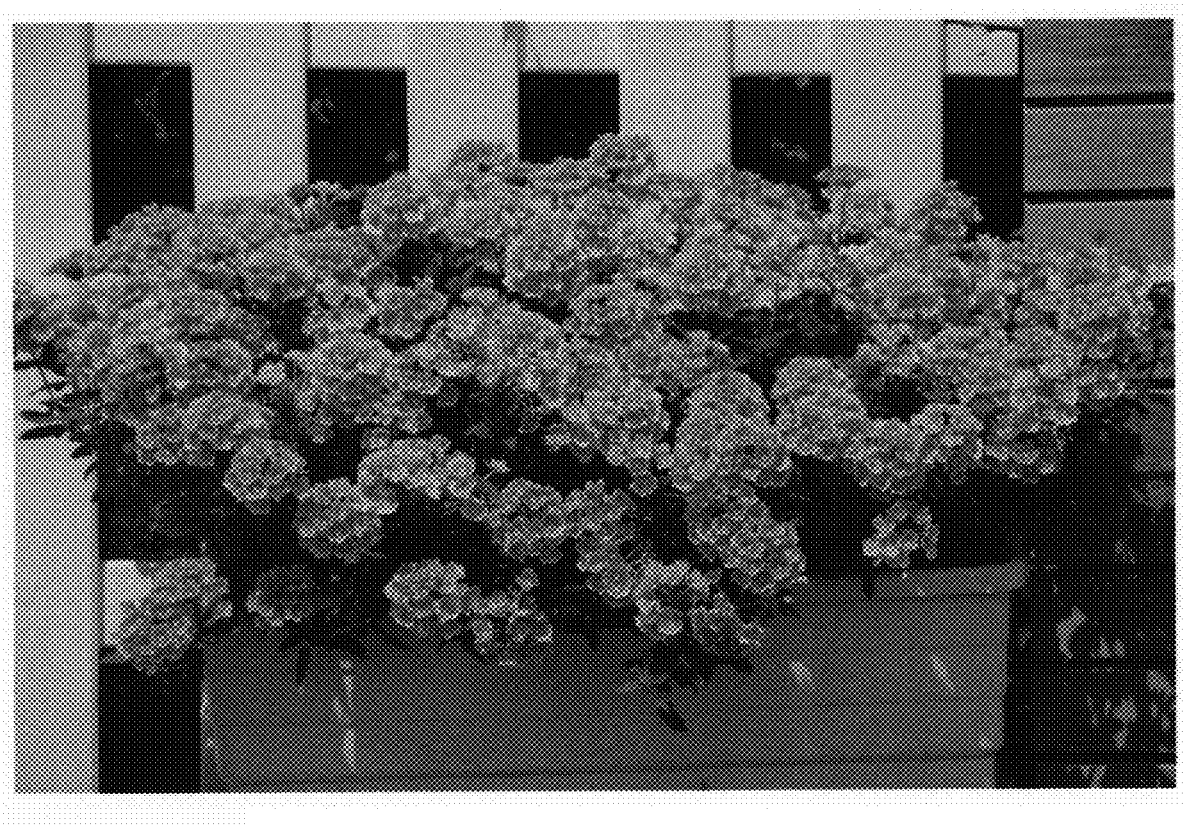

* * * * *